US012653543B2

(12) United States Patent
Sun et al.

(10) Patent No.: US 12,653,543 B2
(45) Date of Patent: Jun. 16, 2026

(54) CLIP CARTRIDGE AND CLIP APPLIER

(71) Applicant: FULBRIGHT MEDICAL INC.,
Jiangyin City Wuxi (CN)

(72) Inventors: Baofeng Sun, Jiangyin City Wuxi
(CN); Tao Cheng, Jiangyin City Wuxi
(CN); Zhichen Qiao, Jiangyin City
Wuxi (CN)

(73) Assignee: FULBRIGHT MEDICAL INC.,
Jiangyin City Wuxi (CN)

( * ) Notice: Subject to any disclaimer, the term of this
patent is extended or adjusted under 35
U.S.C. 154(b) by 199 days.

(21) Appl. No.: 18/719,138

(22) PCT Filed: Dec. 29, 2022

(86) PCT No.: PCT/CN2022/143619
§ 371 (c)(1),
(2) Date: Jun. 12, 2024

(87) PCT Pub. No.: WO2023/125862
PCT Pub. Date: Jul. 6, 2023

(65) Prior Publication Data
US 2025/0049441 A1 Feb. 13, 2025

(30) Foreign Application Priority Data

Dec. 31, 2021 (CN) .......................... 202111670812.3

(51) Int. Cl.
*A61B 17/122* (2006.01)
*A61B 17/08* (2006.01)
*A61B 17/128* (2006.01)
(52) U.S. Cl.
CPC ........ *A61B 17/1222* (2013.01); *A61B 17/083*
(2013.01); *A61B 17/1285* (2013.01)

(58) Field of Classification Search
CPC . A61B 17/105; A61B 17/1222; A61B 17/083;
A61B 17/08; A61B 17/122;
(Continued)

(56) References Cited

U.S. PATENT DOCUMENTS

| | | | |
|---|---|---|---|
| 4,569,469 A | 2/1986 | Mongeon et al. | |
| 5,156,315 A | 10/1992 | Green et al. | |

(Continued)

FOREIGN PATENT DOCUMENTS

| | | |
|---|---|---|
| CN | 104394783 A | 3/2015 |
| CN | 111248972 A | 6/2020 |

(Continued)

OTHER PUBLICATIONS

Office Action for Australia Application No. 2022425321, Mailing
Date: May 29, 2025.

(Continued)

*Primary Examiner* — Majid Jamialahmadi
(74) *Attorney, Agent, or Firm* — MLO, a professional
corp.

(57) ABSTRACT

A clip cartridge and a clip applier are provided. The clip
cartridge includes at least two clips, wherein each of the at
least two clips includes a clip leg, the clip leg has a
protruding portion, the clip cartridge further includes: a clip
cartridge body, wherein the clip cartridge body has a clip
cavity to receive the clips, the at least two clips are stacked
in a first direction in a staggered manner, so that protruding
portions of adjacent clips are staggered in the first direction,
each clip is arranged substantially in a second direction.

20 Claims, 10 Drawing Sheets

(58) Field of Classification Search
CPC ... A61B 17/1227; A61B 17/10; A61B 17/128;
A61B 2017/0688; A61B 2017/0682;
B25C 1/005; B25C 1/001
See application file for complete search history.

(56) References Cited

U.S. PATENT DOCUMENTS

| | | | |
|---|---|---|---|
| 8,485,410 B1 * | 7/2013 | Harshman | B25C 1/001 |
| | | | 411/442 |
| 2012/0029534 A1 | 2/2012 | Whitfield et al. | |
| 2017/0157758 A1 | 6/2017 | Howe | |
| 2017/0245857 A1 | 8/2017 | Shelton, IV et al. | |
| 2019/0125351 A1 | 5/2019 | Qian et al. | |
| 2019/0125352 A1 | 5/2019 | Shelton, IV et al. | |
| 2019/0125355 A1 | 5/2019 | Shelton, IV et al. | |

| | | | |
|---|---|---|---|
| 2019/0231350 A1 | 8/2019 | Scott et al. | |
| 2019/0247046 A1 | 8/2019 | Houser et al. | |
| 2023/0020577 A1 | 1/2023 | Kerver et al. | |

FOREIGN PATENT DOCUMENTS

| | | |
|---|---|---|
| WO | 2021078068 A1 | 4/2021 |
| WO | 2021141971 A1 | 7/2021 |
| WO | 2022182759 A1 | 9/2022 |
| WO | 2023125862 A1 | 7/2023 |

OTHER PUBLICATIONS

Extended European Search Report for EP Application No. 22915111.3 mailed on Nov. 3, 2025.
Office Action for Chinese Patent Application No. 2021116708123 mailed on Sep. 2, 2025.

* cited by examiner

CLIP CARTRIDGE AND CLIP APPLIER

The present disclosure claims priority of the patent application entitled "Clip cartridge and Clip applier" filed to the China National Intellectual Property Administration on Dec. 31, 2021, with the application Ser. No. 202111670812.3, the disclosure of which is incorporated herein by reference in its entirety.

TECHNICAL FIELD

The present disclosure relates to a field of medical device technologies, and more particularly, to a clip cartridge and a clip applier.

BACKGROUND

A clip applier includes a handle assembly, a rod assembly extending from the handle assembly, and a jaw assembly arranged at a distal end of the rod assembly. The rod assembly is provided therein with a clip cartridge for placing clips; For continuous clip applying, the clip cartridge usually has a plurality of clips. During clip applying, by actuating the handle assembly of the clip applier, a clip inside the clip cartridge is pushed into the jaw assembly, and then the jaw assembly is closed, so that the clip located in the jaw assembly clamps onto tissue or a blood vessel, thereby playing a role in hemostasis and ligation closure.

Referring to FIG. 17, there is a clip cartridge in the prior art, clips 1 are arranged within a clip cartridge 2 in a stacked manner, and the clips 1 are not staggered. The clip cartridge 2 is only applicable to a clip 1 having no protruding portion on a clip leg. Referring to FIG. 6, the clip 1 according to the present disclosure includes a clip leg, the clip leg has a protruding portion thereon; if the clips shown in FIG. 6 are arranged according to the placement method in FIG. 17, it will take up a lot of space and it is difficult for the clips to be stably placed in the clip cartridge.

Accordingly, it is necessary to improve the clip cartridge in the prior art.

SUMMARY

With respect to the shortcomings of the existing art, the present disclosure aims to provide a clip cartridge and a clip applier, which solves the problem of large space occupied by the clip cartridge and poor stability of the clips placed inside the clip cartridge.

The present disclosure is realized by the following solution.

A clip cartridge includes at least two clips, each of the at least two clips includes a clip leg, the clip leg has a protruding portion, characterized in that the clip cartridge further includes: a clip cartridge body, the clip cartridge body has a clip cavity to receive the clips, the at least two clips are stacked in a first direction in a staggered manner, so that protruding portions of adjacent clips are staggered in the first direction, each clip is arranged substantially in a second direction.

In one embodiment, each clip leg has two sidewalls opposite to each other in the first direction, and at least one of the sidewalls has the protruding portion.

In one embodiment, the clip cartridge further includes a bias assembly, the bias assembly is arranged in the clip cartridge body, and the bias assembly applies a force on the clip substantially in the first direction.

In one embodiment, the clip cavity includes a first cavity and a second cavity that are sequentially arranged in the first direction, and in an initial state, both the first cavity and the second cavity receive the clips.

In one embodiment, the bias assembly includes an elastic member.

In one embodiment, the bias assembly abuts against a first clip in a forward direction along the first direction.

In one embodiment, the clip leg has two sidewalls opposite to each other in the first direction, at least one of the sidewalls is provided with the protruding portion, each of the clips includes a first end portion and a second end portion, the protruding portion is close to the first end portion and away from the second end portion, the first cavity is provided therein with a position limiting slope, and the position limiting slope abuts against the second end portion of the clip in the first cavity.

In one embodiment, the clip leg has two sidewalls opposite to each other in the first direction, at least one of the sidewalls is provided thereon with the protruding portion, the second cavity has a groove extending in the second direction, and the protruding portion of the clip located in the second cavity is received in the groove.

In one embodiment, the clip cartridge has a first end and a second end opposite to each other in the second direction, the second cavity extends in the second direction, the second cavity forms a first opening at the first end of the clip cartridge, and the second cavity forms a second opening at the second end of the clip cartridge.

In one embodiment, the clip cartridge body includes a position limiting member, the position limiting member is arranged on a sidewall of the clip cartridge body, the position limiting member abuts against the clip located in the second cavity, and in response to a force applied in the second direction on the clip, the clip detaches from the position limiting member and detaches from the second cavity at the first opening.

Moreover, the present disclosure provides a clip applier, the clip applier includes a handle assembly, a rod assembly, and a jaw assembly, the rod assembly extends from the handle assembly, the jaw assembly is provided at a distal end of the rod assembly, characterized in that the clip applier further includes the clip cartridge, and the clip cartridge is provided at the rod assembly. Further, the clip cartridge is connected with the rod assembly through a buckle structure.

As compared with the existing art, advantageous effects of the present disclosure are as follows: in the clip cartridge according to the present disclosure, the clips are stacked in a staggered manner, which can save space, so that the space occupied by the clip cartridge is small; protruding portions of adjacent clips can avoid each other, so that the clips can be stably stacked inside the clip cartridge.

REFERENCE NUMERALS OF THE ABOVE FIGURES

Figure 1:
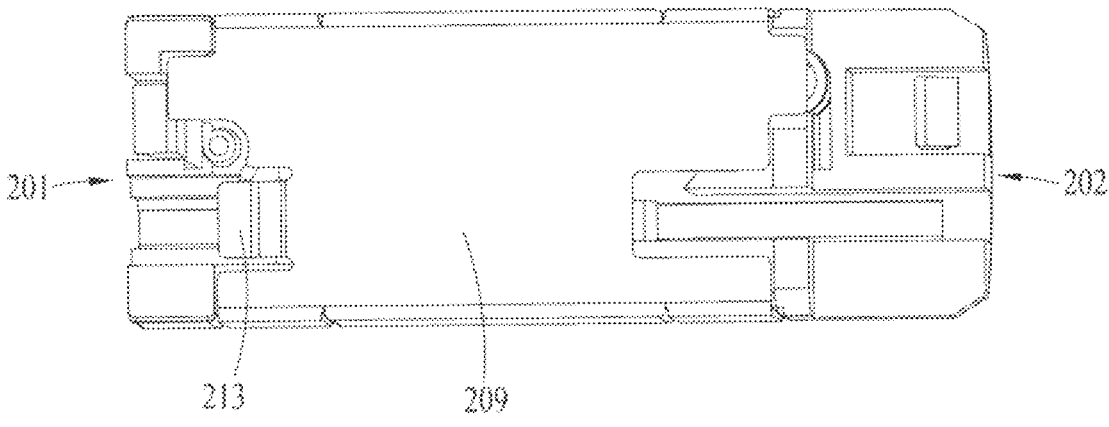
FIG. 1 is a schematic structural view of a clip cartridge at a first angle and provided by a specific embodiment of the present disclosure.

1. clip; 101. clip; 102. clip; 103. clip; 104. first clip leg; 105. second clip leg; 106. first protruding portion; 107. second protruding portion; 108. protruding block; 109. first end portion; 110. second end portion; 111. upper sidewall; 112. lower sidewall; 2. clip cartridge; 201. first end; 202. second end; 203. first cavity; 204. second cavity; 205. first opening; 206. second opening; 207. first groove; 208. second groove; 209. first male buckle; 210. second male buckle; 209. first side portion; 2091. first mounting portion; 2092. second mounting portion; 2093. third mounting portion; 210. second side portion; 211. third side portion; 212. fourth side portion; 213. position limiting member; 214. position limiting slope; 215. mounting block; 216. recess portion; 217. mounting groove; 218. elastic member; 2181. first torsion arm; 2182. second torsion arm; 2183. spiral body; 219. push plate; 3. rod assembly; 301. shaft; 3011. channel; 3012. first female buckle; 3013. second female buckle; 3014. first shaft; 3015. second shaft; 302. feeding rod; 303. sleeve; 3031. first tube; 3032. second tube; 4. jaw assembly; 401. first jaw member; 402. second jaw member; 403. spring; 5. handle assembly; 6. pivot member; 7. joint.

DETAILED DESCRIPTION

In order to make objects, technical solutions and advantages of the present disclosure more clear, the present disclosure will be further illustrated in detail below in combination with the drawings and the embodiments. It should be understood that the specific embodiments descried here are merely used for explaining the present disclosure, and not intended to limit the present disclosure. Based on the embodiments described herein, those ordinarily skilled in the art can obtain other embodiment(s), without any inventive work, which should be within the scope of the present disclosure.

It should be understood that the terms "proximal", "back", "distal", and "front" used herein are relative to a clinical doctor who manipulates a handle assembly of a clip applier. The terms "proximal" and "back" refer to a portion close to the clinical doctor, while the terms "distal" and "front" refer to a portion away from the clinical doctor. That is, the handle assembly is a proximal end, and the jaw assembly is a distal end; for example, a proximal end of a certain component represents an end relatively close to the handle assembly, while a distal end represents an end relatively close to the jaw assembly. However, the clip applier may be used in many directions and positions, so these terms that express relative positional relationships are not limited or absolute.

In the present disclosure, unless otherwise clearly specified and limited, the terms such as "connected" and "connection" should be broadly understood, for example, it may be fixed connection, or detachable connection, or movable connection; or may also be direct connection, or may also be indirect connection through an intermediate medium, or may also be internal communication of two elements or interaction relationship between two elements such as abut connection. Those ordinarily skilled in the art may understand the specific meanings of the above-described terms in the present disclosure according to specific situations. It should be noted that when a qualifier is used before the terms such as "connected" and "connection", it has a meaning limited by the corresponding qualifier, which only excludes situations that clearly need to be excluded, and does not exclude other possible situations.

Taking a direction and an angle for placing the clip cartridge 2 in FIG. 1 as reference, the clip cartridge 2 in FIG. 1 is placed in a horizontal direction; a first direction is an up-down direction (i.e., a vertical direction), and a forward direction of the first direction is from top to bottom; a second direction is a longitudinal direction of the clip cartridge 2, which is a left-right direction, that is, a horizontal direction. A third direction is a direction perpendicular to a paper surface; and the first direction, the second direction, and the third direction are perpendicular to each other. It should be noted that when taking the direction and the angle for placing the clip cartridge 2 in FIG. 1 as reference, the third direction is perpendicular to the paper surface; however, once the direction and the angle for placing the clip cartridge 2 change in other figures, the third direction changes with the direction and the angle of the clip cartridge 2.

Please refer to FIG. 1 to FIG. 4, the present disclosure provides a clip cartridge 2, which includes at least two clips 1. The clip 1 according to the present disclosure is a commonly used surgical clip in the existing art. The clip 1 includes a clip leg; and the clip leg has a protruding portion. The clip cartridge 2 includes a clip cartridge body; and the clip cartridge body has a clip cavity therein to receive the clip 1. The at least two clips 1 are stacked in a first direction in a staggered manner, so that protruding portions of adjacent clips are staggered (i.e., are not overlapped with each other) in the first direction. Each clip 1 is arranged substantially in a second direction. By placing the clips 1 in a stacked manner, space can be saved, so that space occupied by the clip cartridge 2 is smaller. By placing the clips 1 in a staggered manner, protruding portions of adjacent clips can avoid each other, which can further reduce space occupied by the clips, and allow the clips 1 to be stably stacked in the clip cartridge 2 without tipping over.

Figure 5:
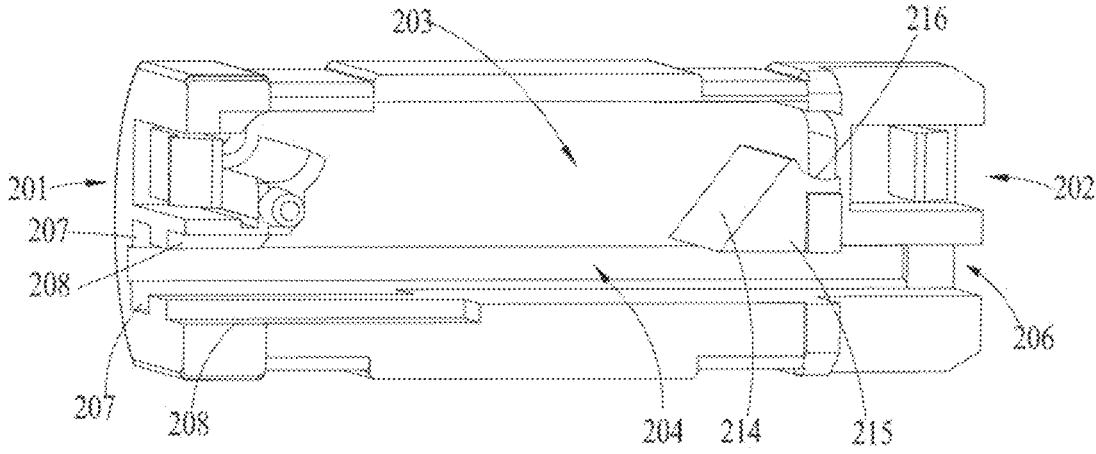
FIG. 5 is a schematic structural view of a clip cartridge body provided by a specific embodiment of the present disclosure, in which the first side portion is not shown.

Referring to FIG. 5, in this embodiment, the clip cavity inside the clip cartridge body includes a first cavity 203 and a second cavity 204. The first cavity 203 and the second cavity 204 are sequentially arranged in the first direction, that is, the first cavity 203 is arranged above the second cavity 204. The first cavity 203 is in communication with the second cavity 204.

Figure 4:
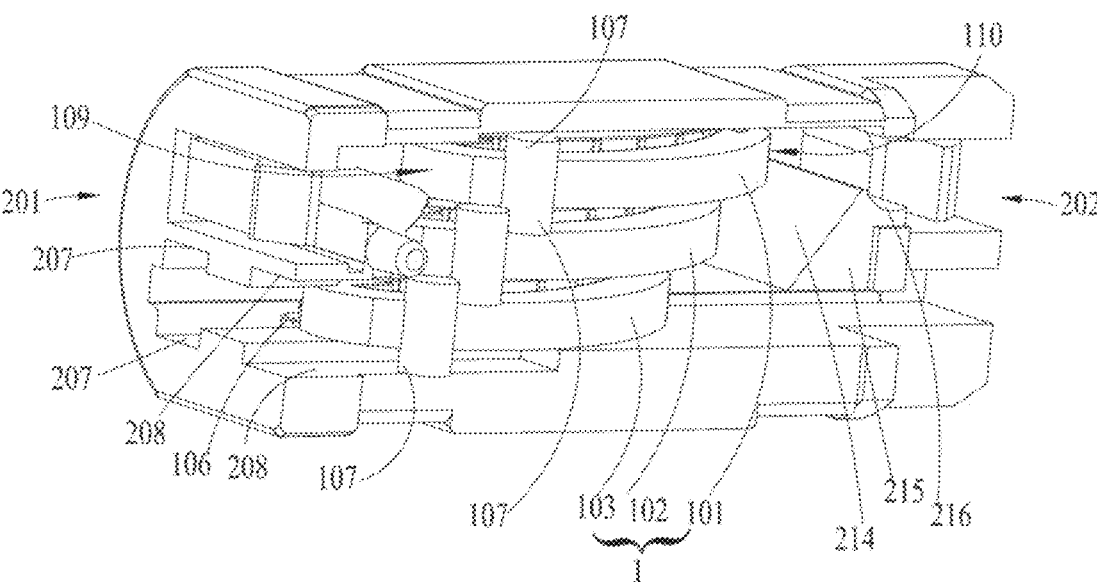
FIG. 4 is a schematic structural view of the clip cartridge at a fourth angle and provided by a specific embodiment of the present disclosure, in which neither the first side portion nor a bias assembly are shown.

Referring to FIG. 4, the clip cartridge 2 includes three clips 1, namely, clip 101, clip 102 and clip 103 sequentially arranged from top to bottom. In an initial state, the clip 101 and the clip 102 are arranged in the first cavity 203; the clip 103 is arranged in the second cavity 204; the number of clips 1 will not affect normal use of the clip cartridge 2, and an operator can also adjust the number of clips 1 according to specific requirements.

Figure 6:
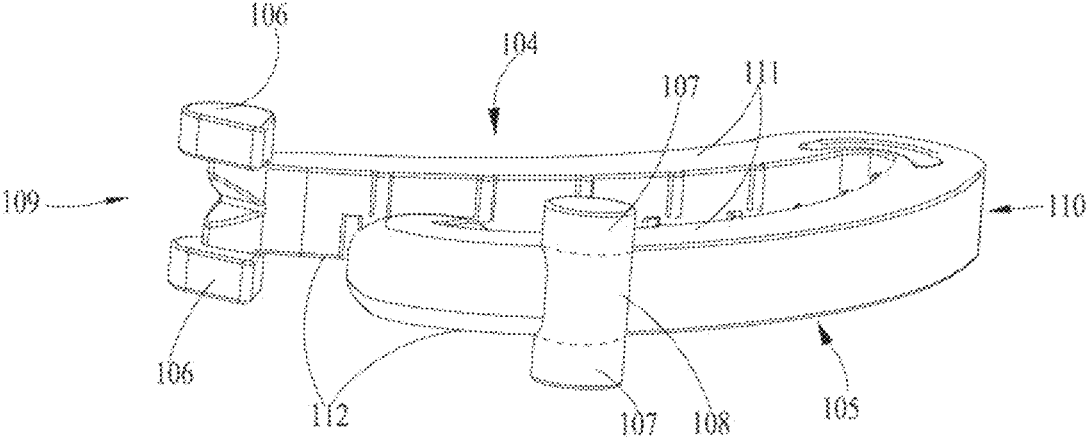
FIG. 6 is a schematic structural view of a clip provided by a specific embodiment of the present disclosure.

Referring to FIG. 6, the clip 1 includes two clip legs, namely, a first clip leg 104 and a second clip leg 105. The first clip leg 104 of the clip 1 has an upper sidewall 111 and a lower sidewall 112 opposite to each other in the first direction; the upper sidewall 111 of the first clip leg 104 has a first protruding portion 106, and the lower sidewall 112 of the first clip leg 104 also has a first protruding portion 106. The second clip leg 105 has an upper sidewall 111 and a lower sidewall 112 opposite to each other in the first direction. The upper sidewall 111 of the second clip leg 105 has a second protruding portion 107; and the lower sidewall 112 of the second clip leg 105 also has a second protruding portion 107. The two second protruding portions 107 are connected with each other through a protruding block 108. Specifically, a lower end of the second protruding portion 107 of the upper sidewall 111 of the second clip leg 105 is connected with an upper end of the second protruding portion 107 of the lower sidewall 112 of the second clip leg 105 through the protruding block 108. In this embodiment, the two second protruding portions 107 and the protruding block 108 are integrated to facilitate processing. In other embodiments, the protruding block 108 that is in the middle may also be omitted.

Figure 7:
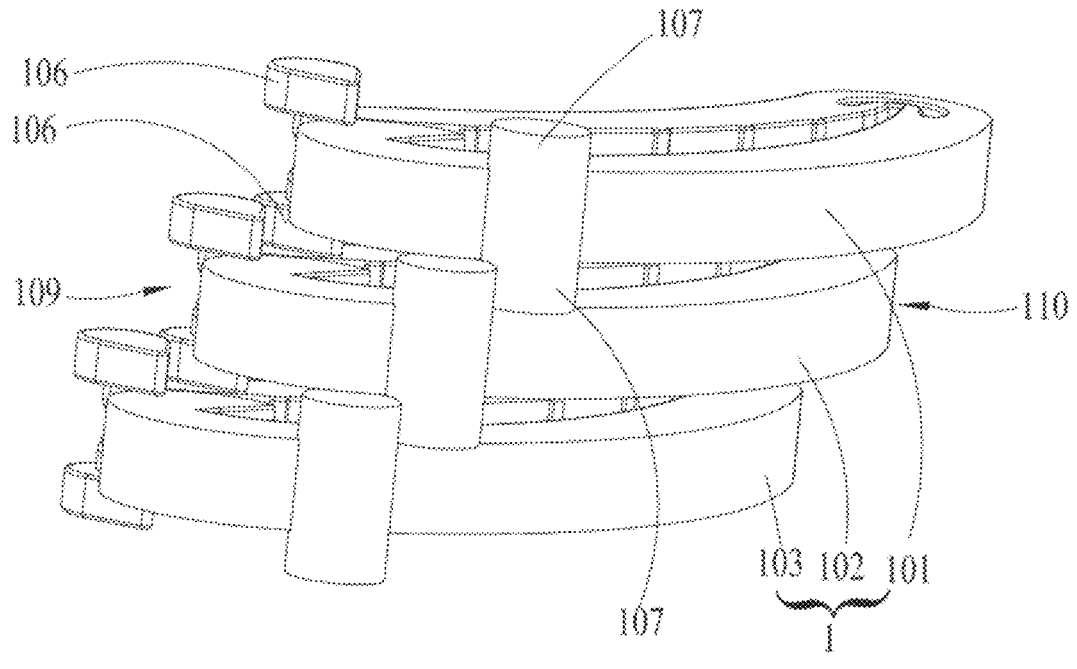
FIG. 7 is a schematic view of stacking of clips in the clip cartridge body provided by a specific embodiment of the present disclosure.

Referring to FIG. 5 to FIG. 7, the clip cartridge 2 has a first end 201 and a second end 202 opposite to each other in the second direction. It should be noted that the first end 201 is a region rather than an endpoint, and the second end 202 is also a region rather than an endpoint. The clip 1 has a first end portion 109 and a second end portion 110 opposite to each other in the second direction. Similarly, the first end portion 109 is a region rather than an endpoint, and the second end portion 110 is a region rather than an endpoint. The first end portion 109 of the clip 1 is close to the first end 201 of the clip cartridge 2; and the second end portion 110 of the clip 1 is close to the second end 202 of the clip cartridge 2. Each first protruding portion 106 and each second protruding portion 107 of the clip 1 are both close to the first end portion 109 of the clip 1 and away from the second end portion 110 of the clip 1. Preferably, each first protruding portion 106 of the clip 1 is located at the first end portion 109.

With emphasized reference to FIG. 3 to FIG. 4, and FIG. 7, a stacking mode of the clips 1 within the clip cartridge 2 is as follows.

A first protruding portion 106 and a second protruding portion 107 on a lower sidewall of the clip 101 both abut against an upper sidewall of the clip 102; and a second protruding portion 107 on the upper sidewall of the clip 102 abuts against the lower sidewall of the clip 101. More specifically, the first protruding portion 106 on the lower sidewall of the first clip leg 104 of the clip 101 abuts against the upper sidewall of the first clip leg 104 of the clip 102; and the second protruding portion 107 on the lower sidewall of the second clip leg 105 of the clip 101 abuts against the upper sidewall of the second clip leg 105 of the clip 102. The second protruding portion 107 on the upper sidewall of the second clip leg 105 of the clip 102 abuts against the lower sidewall of the second clip leg 105 of the clip 101.

A first protruding portion 106 and a second protruding portion 107 on a lower sidewall of the clip 102 both abut against an upper sidewall of the clip 103, while a second protruding portion 107 on the upper sidewall of the clip 103 abuts against the lower sidewall of the clip 102. More specifically, the first protruding portion 106 on the lower sidewall of the first clip leg 104 of the clip 102 abuts against the upper sidewall of the first clip leg 104 of the clip 103; and the second protruding portion 107 on the lower sidewall of the second clip leg 105 of the clip 102 abuts against the upper sidewall of the second clip leg 105 of the clip 103. The second protruding portion 107 on the upper sidewall of the second clip leg 105 of the clip 103 abuts against the lower sidewall of the second clip leg 105 of the clip 102.

In summary, clip 101, clip 102 and clip 103 are stacked in the first direction, which can save space and make the space occupied by the clip cartridge 2 smaller. The first protruding portion 106 of the clip 102 is staggered with the first protruding portion 106 of the clip 101; and the second protruding portion 107 of the clip 102 is also staggered with the second protruding portion 107 of the clip 101. The first protruding portion 106 of the clip 103 is staggered with the first protruding portion 106 of the clip 102; and the second protruding portion 107 of the clip 103 is also staggered with the second protruding portion 107 of the clip 102. Moreover, the first protruding portion 106 of the clip 102 and the first protruding portion 106 of the clip 101 have no overlapping portion in the first direction; and the second protruding portion 107 of the clip 102 and the second protruding portion 107 of the clip 101 have no overlapping portion in the first direction. The first protruding portion 106 of the clip 103 and the first protruding portion 106 of the clip 102 have no overlapping portion in the first direction, and the second protruding portion 107 of the clip 103 and the second protruding portion 107 of the clip 102 have no overlapping portion in the first direction, so that adjacent protruding portions can avoid each other, which further reduces space occupied by the clips 1, and the clips 1 can be stably stacked in the clip cartridge 2 without tipping over.

Figure 3:
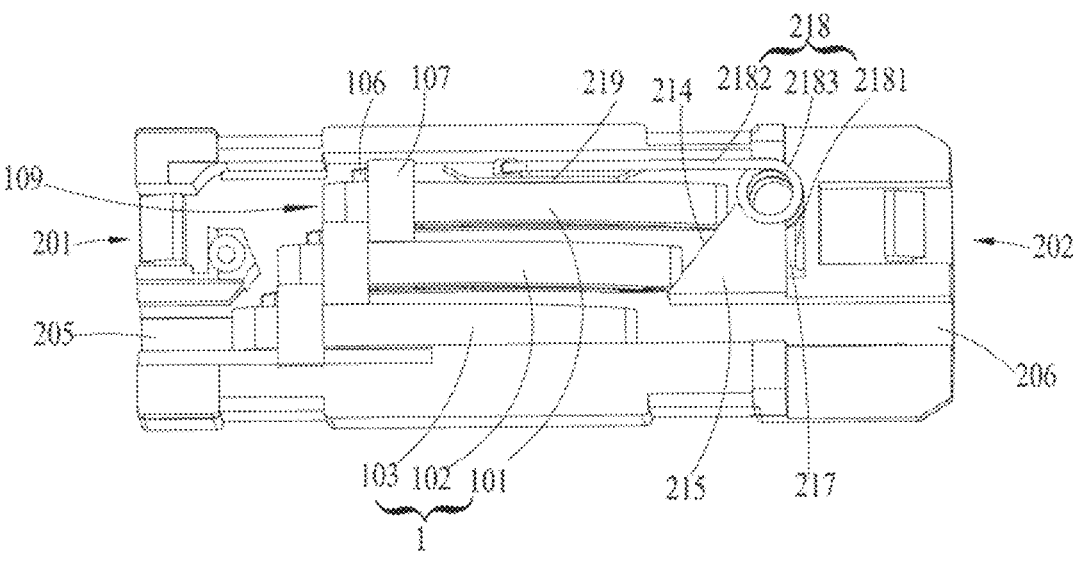
FIG. 3 is a schematic structural view of the clip cartridge at a third angle and provided by a specific embodiment of the present disclosure, in which a first side portion is not shown.
Figure 8:
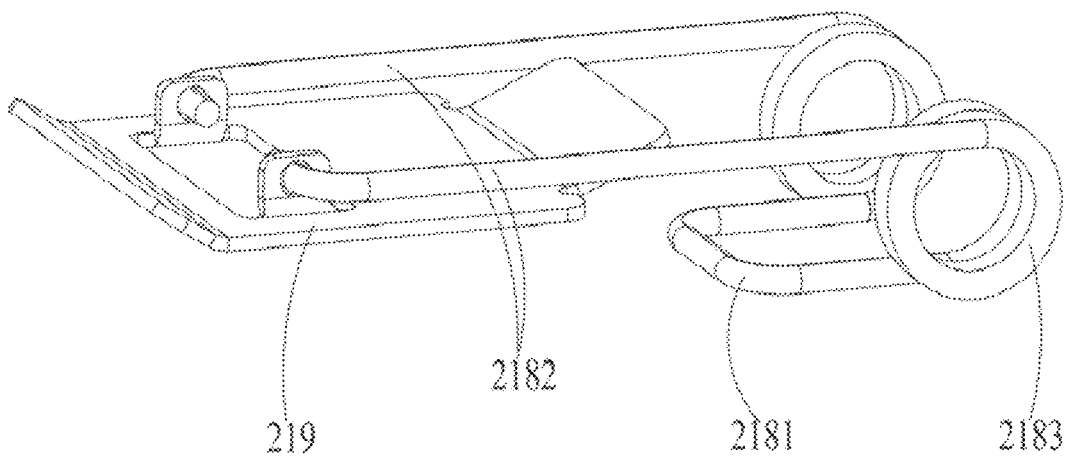
FIG. 8 is a schematic structural view of a bias assembly provided by a specific embodiment of the present disclosure.

Referring to FIG. 3 and FIG. 8, the clip cartridge 2 further includes a bias assembly; and the bias assembly is arranged in the clip cartridge body. Specifically, the bias assembly is arranged in the first cavity 203 of the clip cartridge body.

The bias assembly can apply a force on the clip 1 substantially in the first direction, so that the clip 1 in the first cavity 203 can enter the second cavity 204. The above-described force also helps the clip 1 be stably maintained in the clip cartridge 2.

Specifically, the bias assembly includes an elastic member 218 and a push plate 219. The push plate 219 abuts against the upper sidewall of the clip 101; and the push plate 219 can be rigid or at least substantially rigid. Owing to the elastic member 218, the push plate 219 can apply force on the clip 101 in the first direction. In this embodiment, the elastic member 218 is selected as a torsion spring. for example, the elastic member 218 includes a first torsion arm 2181, a second torsion arm 2182, and a spiral body 2183. The first torsion arm 2181, the second torsion arm 2182, and the spiral body 2183 are integrated. Referring to FIG. 8, without external force, the first torsion arm 2181 and the second torsion arm 2182 of the clastic member 218 are both in a natural stretching state.

Referring to FIG. 3, a mounting block 215 is provided within the first cavity 203 for mounting the clastic member 218. The position of the elastic member 218 will not affect the function thereof on the clip 1, so the mounting block 215 can be arranged in any position of the first cavity 203. But in order to save space and facilitate arrangement of the clips 1 in the first cavity 203, the mounting block 215 is arranged close to the first end 201 or the second end 202 of the clip cartridge 2. In this embodiment, the mounting block 215 is arranged close to the second end 202 of the clip cartridge 2.

The mounting block 215 has a recess portion 216 fit with the spiral body 2183; and the spiral body 2183 is disposed on the recess portion 216. The mounting block 215 is further provided with a mounting groove 217. The first torsion arm 2181 is arranged inside the mounting groove 217; and the second torsion arm 2182 is twisted by a certain angle around the spiral body 2183 and then is arranged on an upper side of the clip 101 and connected with the push plate 219, causing the elastic member 218 to deform. Therefore, the second torsion arm 2182 can apply the force on the clip 101 substantially in the first direction through the push plate 219.

Referring to FIG. 3 to FIG. 5, in this embodiment, the second cavity 204 extends through the clip cartridge body. Specifically, the second cavity 204 extends in the second direction; the second cavity 204 forms a first opening 205 at the first end 201 of the clip cartridge 2; and the second cavity 204 forms a second opening 206 at the second end 202 of the clip cartridge 2. In response to the force applied to the clip 103 in the second direction, the clip 103 detaches from the clip cartridge 2 via the first opening 205, and the bias assembly pushes the clip 101 and the clip 102 downwards, allowing the clip 102 to enter the second cavity 204. After the clip 102 detaches from the clip cartridge 2, the bias assembly further pushes the clip 101 into the second cavity 204.

Referring to FIG. 3 to FIG. 4, and FIG. 7, the first protruding portion 106 of the clip 102 is closer to the first end 201 of the clip cartridge 2 than the first protruding portion 106 of the clip 101; and the second protruding portion 107 of the clip 102 is closer to the first end 201 of the clip cartridge 2 than the second protruding portion 107 of the clip 101. Therefore, when the clip 102 moves towards the first end 201 of the clip cartridge 2, the first protruding portion 106 and second protruding portion 107 of the clip 101 will not interrupt the movement of the clip 102.

The first protruding portion 106 of the clip 103 is closer to the first end 201 of the clip cartridge 2 than the first protruding portion 106 of the clip 102. The second protruding portion 107 of the clip 103 is closer to the first end 201 of the clip cartridge 2 than the second protruding portion 107 of the clip 102. Therefore, when the clip 103 moves towards the first end 201 of the clip cartridge 2, the first protruding portion 106 and the second protruding portion 107 of the clip 102 will not interrupt movement of the clip 103.

With respect to the three clips 1 in the clip cartridge body, the first end portions 109 thereof are not aligned in the first direction; the first end portion 109 of the clip 101 is farthest away from the first end 201 of the clip cartridge 2; and the first end portion 109 of the clip 103 is closest to the first end 201 of the clip cartridge 2. Similarly, the second end portions 110 of the three clips 1 are not aligned in the first direction. The second end portion 110 of the clip 101 is closest to the second end 202 of the clip cartridge 2; and the second end portion 110 of the clip 103 is farthest away from the second end 202 of the clip cartridge 2. Referring to FIG. 3 to FIG. 5, a position limiting slope 214 is arranged in the first cavity 203; and the position limiting slope 214 abuts against the second end portion 110 of the clip 1 in the first cavity 203. Therefore, the position limiting slope 214 can support the clip 1 inside the first cavity 203. That is, the first end portion 109 of the clip 101 is supported on the clip 102. Specifically, the first end portion 109 of the clip 101 is supported on the clip 102 through the first protruding portion 106 and the second protruding portion 107 of the lower sidewall thereof; and the second end portion 110 of the clip 101 is supported on the position limiting slope 214. The first end portion 109 of the clip 102 is supported on the clip 103. Specifically, the first end portion 109 of the clip 102 is supported on the clip 103 through the first protruding portion 106 and the second protruding portion 107 of the lower sidewall thereof, and the second end portion 110 of the clip 102 is supported on the position limiting slope 214. In this embodiment, preferably, the position limiting slope 214 is arranged on the mounting block 215, which can further save space; and in this case, the mounting block 215 is arranged adjacent to the second end 202 of the clip cartridge 2.

Figure 2:
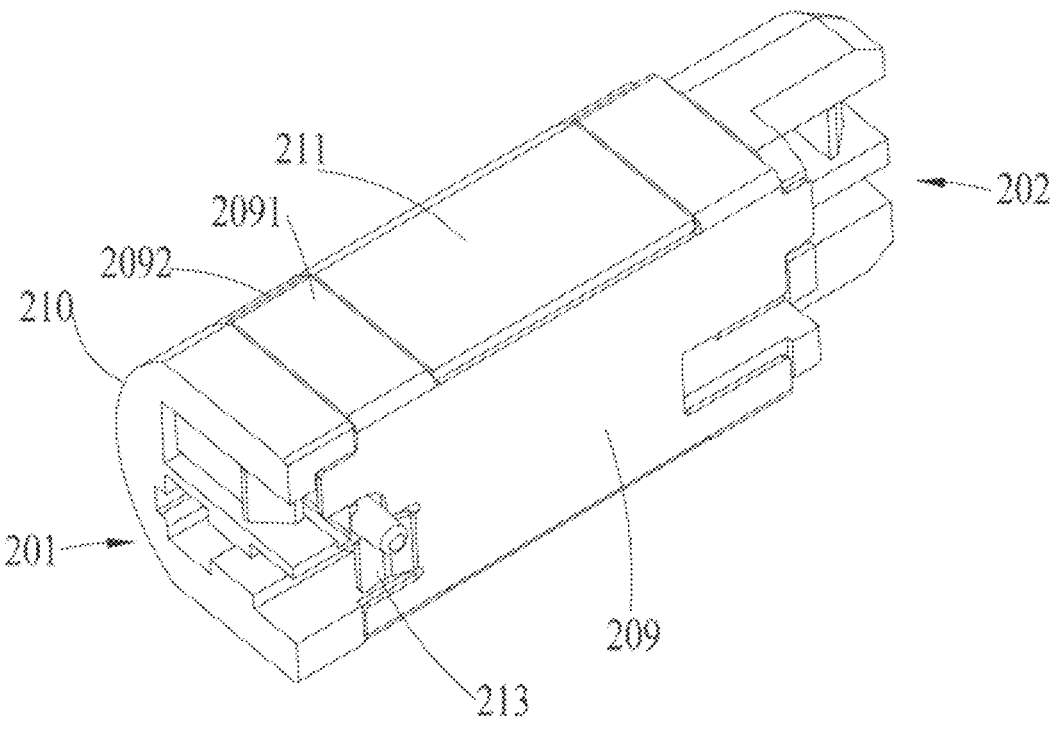
FIG. 2 is a schematic structural view of the clip cartridge at a second angle and provided by a specific embodiment of the present disclosure.
Figure 9:
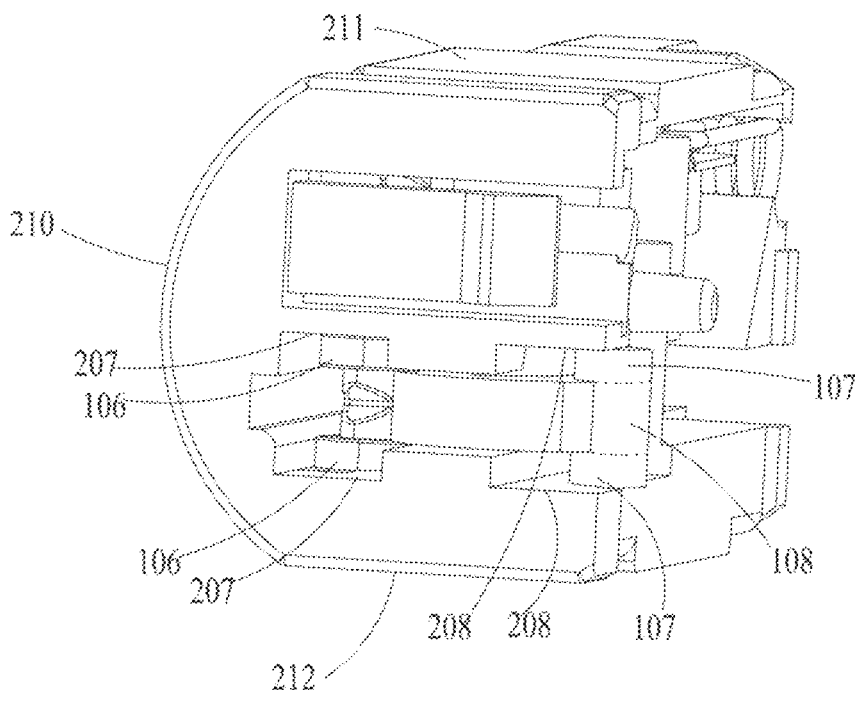
FIG. 9 is a schematic structural view of the clip cartridge at a fifth angle and provided by a specific embodiment of the present disclosure, in which the first side portion is not shown.

Referring to FIG. 1 to FIG. 2, and FIG. 9, in this embodiment, the clip cartridge body has a first side portion 209 and a second side portion 210 opposite to each other in the third direction. The clip cartridge body has a third side portion 211 and a fourth side portion 212 opposite to each other in the first direction. Referring to FIG. 1 to FIG. 2, and FIG. 10 to FIG. 11, the clip cartridge body further includes a position limiting member 213; and the position limiting member 213 is elastic. The position limiting member 213 is provided at the first side portion 209 of the clip cartridge body; and the position limiting member 213 is provided in the second cavity 204. The position limiting member 213 abuts against the clip 1 located in the second cavity 204.

s described above, the lower end of the second protruding portion 107 on the upper sidewall of the second clip leg 105 of the clip 1 is connected with the upper end of the second protruding portion 107 on the lower sidewall of the second clip leg 105 through the protruding block 108. The position limiting member 213 abuts against the protruding block 108 of the clip 1 located in the second cavity 204. In response to the force applied to the clip 1 in the second direction, the protruding block 108 of the clip 1 in the second cavity 204 detaches from the position limiting member 213, and the clip 1 detaches from the second cavity 204 via the first opening 205. The position limiting member 213 can also abut against the second protruding portion 107 of the clip 1 for position limiting.

In this embodiment, by providing the bias assembly, the clip 1 can be stably maintained in the clip cavity. By providing the position limiting member 213 and the position limiting slope 214, the clip 1 can be further limited in position, so that the clip 1 is placed more stably in the clip cavity. Referring to FIG. 1 to FIG. 4, and FIG. 9 to FIG. 11, the position limiting member 213 extends in the second direction and is recessed towards the clip cavity, therefore the position limiting member 213 can apply a force substantially in the second direction and towards the second end 202 of the clip cartridge on the protruding block 108 of the clip 103; the second protruding portion 107 of the upper sidewall of the clip 103 abuts against the second protruding portion 107 of the lower sidewall of the clip 102 substantially in the second direction; because the second protruding portion 107 of the upper sidewall of the clip 102 abuts against the second protruding portion 107 of the lower sidewall of the clip 101 substantially in the second direction, and the second end portion 110 of the clip 102 abuts against the position limiting slope 214, the second end portion 110 of the clip 101 also abuts against the position limiting slope 214. Therefore, the clip 102 can cooperate with the position limiting member 213 to produce position limitation of the clip 103. Meanwhile, the clip 103 cooperates with the position limiting slope 214 to produce position limitation of the clip 102, and the clip 102 cooperates with the position limiting slope 214 to produce position limitation of the clip 101. Therefore, the clip 101, the clip 102 and the clip 103 have a position limit effect on each other in the second direction. Meanwhile, the first end portion 109 of the clip 101 is supported on the clip 102, and the second end portion 110 of the clip 101 is supported on the position limiting slope 214. The first end portion 109 of the clip 102 is supported on the clip 103, and the second end portion 110 of the clip 102 is supported on the position limiting slope 214; and the bias assembly applies a force substantially in the first direction on the clip 1, so that the clips 1 are stably maintained in the clip cavity of the clip cartridge. The clip 101 can be arranged substantially in the second direction. The clip 102 can also be arranged substantially in the second direction, and the second end portion 110 of the clip 102 will not fall into the second cavity 204 to affect the use of the clip 103, for which description below can be specifically referred to.

Figure 10:
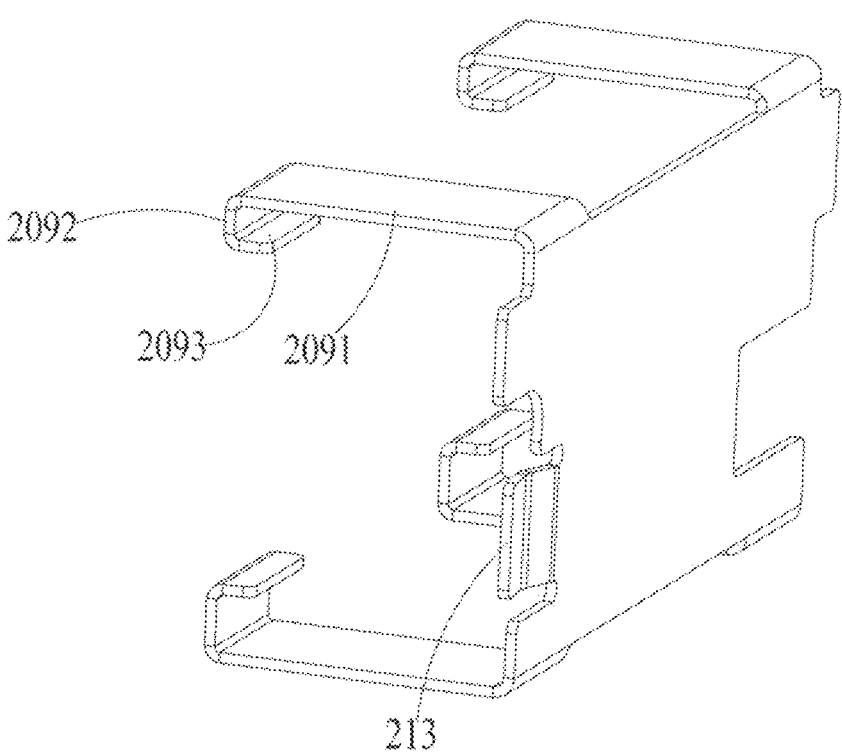
FIG. 10 is a schematic structural view of the first side portion of the clip cartridge provided by a specific embodiment of the present disclosure.
Figure 11:
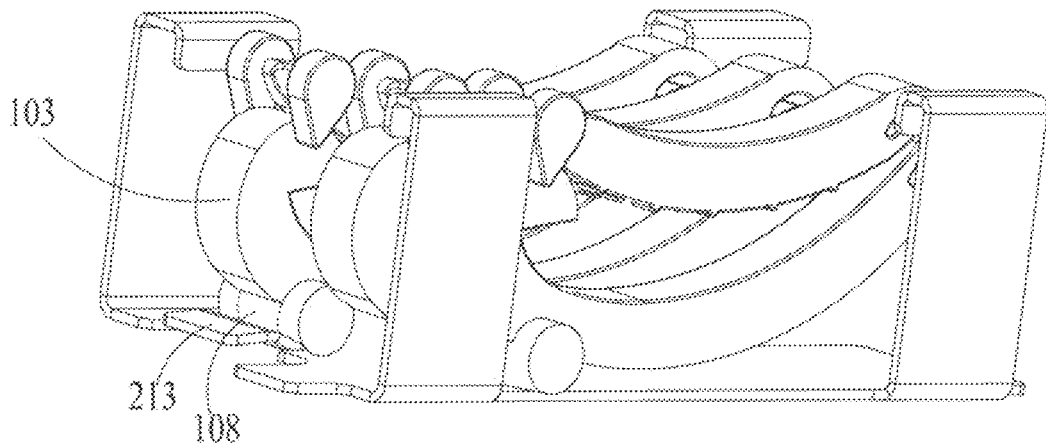
FIG. 11 is a schematic view of a mode of cooperation between the first side portion and the clip provided by a specific embodiment of the present disclosure.

Referring to FIG. 1 to FIG. 2 and FIG. 9 again, in order to facilitate mounting of the clip 1 inside the clip cartridge 2, in this embodiment, the first side portion 209 is arranged to be detachable from the clip cartridge body. Specifically, the first side portion 209 is detachably connected with the clip cartridge body. Referring to FIG. 10, an upper end of the first side portion 209 is provided with two snap pieces, and a lower end of the first side portion 209 is also provided with two snap pieces. Each snap piece includes a first mounting portion 2091, a second mounting portion 2092, and a third mounting portion 2093. Referring to FIG. 2, with respect to each snap piece at the upper end of the first side portion 209, the first mounting portion 2091 is arranged on an outer wall of the third side portion 211, the second mounting portion 2092 is arranged on the outer wall of the second side portion 210, and the third mounting portion 2093 is embedded in the second side portion 210. With respect to each snap piece at the lower end of the second side portion 210, the first mounting portion 2091 is arranged on an outer wall of the fourth side portion 212, the second mounting portion 2092 is arranged on the outer wall of the second side portion 210, and the third mounting portion 2093 is embedded in the second side portion 210.

Referring to FIG. 5 and FIG. 9, the second cavity 204 has a groove extending in the second direction, and the protruding portion of the clip 1 that is located in the second cavity 204 is received in the groove. Specifically, the second cavity 204 has an upper wall portion and a lower wall portion opposite to each other in the first direction; a third opening is arranged at the upper wall portion of the second cavity 204 at a position corresponding to the first cavity 203, that is, the second cavity 204 is in communication with the first cavity 203 through the third opening, so that the clip 1 inside the first cavity 203 can enter the second cavity 204.

An inner wall of the upper wall portion of the second cavity 204 is provided with a first groove 207 and a second groove 208. An inner wall of the lower wall portion of the second cavity 204 is also provided with a first groove 207 and a second groove 208. The first protruding portion 106 on the upper sidewall of the clip 1 is operably located in the first groove 207 of the upper wall portion of the second cavity 204; and the second protruding portion 107 on the upper sidewall of the clip 1 is operably located in the second groove 208 of the upper wall portion of the second cavity 204. The first protruding portion 106 on the lower sidewall of the clip 1 is operably located in the first groove 207 of the lower wall portion of the second cavity 204; and the second protruding portion 107 on the lower sidewall of the clip 1 is operably located in the second groove 208 of the lower wall portion of the second cavity 204. Therefore, the clip 1 can be stably placed in the second cavity 204. Each first groove 207 and each second groove 208 extend through the first end 201 of the clip cartridge 2, so that the clip 1 within the second cavity 204 can stably detach from the clip cartridge 2 at the first end 201 of the clip cartridge 2.

Figure 12:
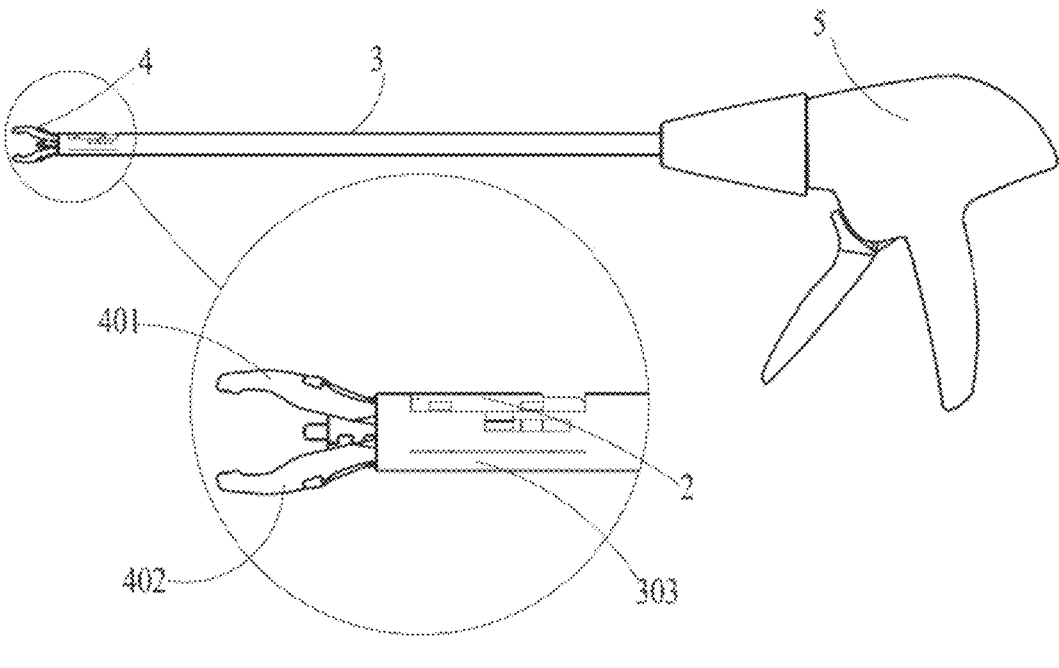
FIG. 12 is a schematic structural view of a clip applier at a first angle and provided by a specific embodiment of the present disclosure.
Figure 14:
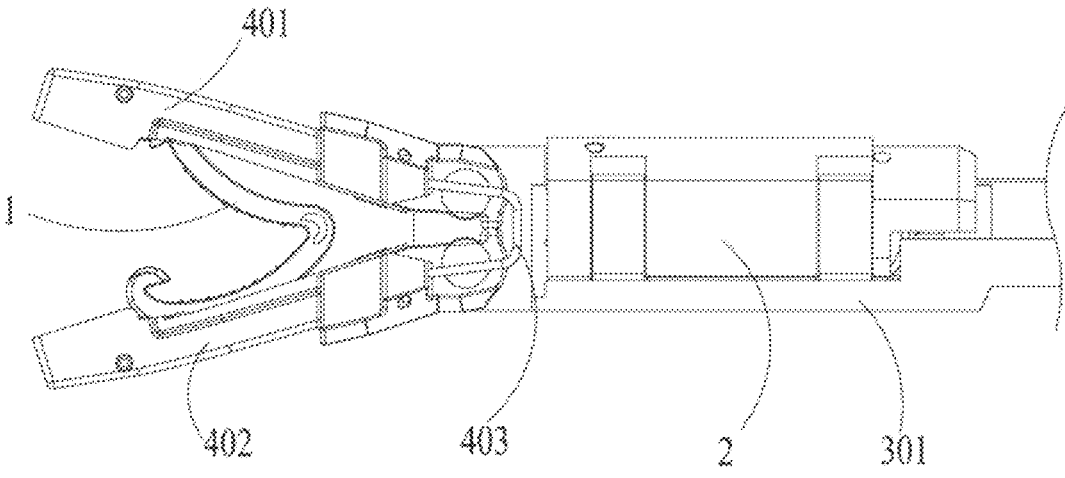
FIG. 14 is a schematic structural view of a partial region of the clip applier provided by a specific embodiment of the present disclosure, in which a sleeve is not shown.

Referring to FIG. 12 and FIG. 14, the present disclosure further provides a clip applier, including a handle assembly 5, a rod assembly 3 extending from the handle assembly 5, and a jaw assembly 4.

The handle assembly 5 is used for operating the clip applier. The jaw assembly 4 is arranged at a distal end of the rod assembly 3.

The rod assembly 3 includes a shaft 301, the clip cartridge 2, a feeding rod 302, and a sleeve 303 sleeved on the shaft 301 and the clip cartridge 2. The shaft 301 has strong rigidity. The jaw assembly 4 includes a first jaw member 401 and a second jaw member 402 that are pivotally connected with the shaft 301, respectively.

Figure 13:
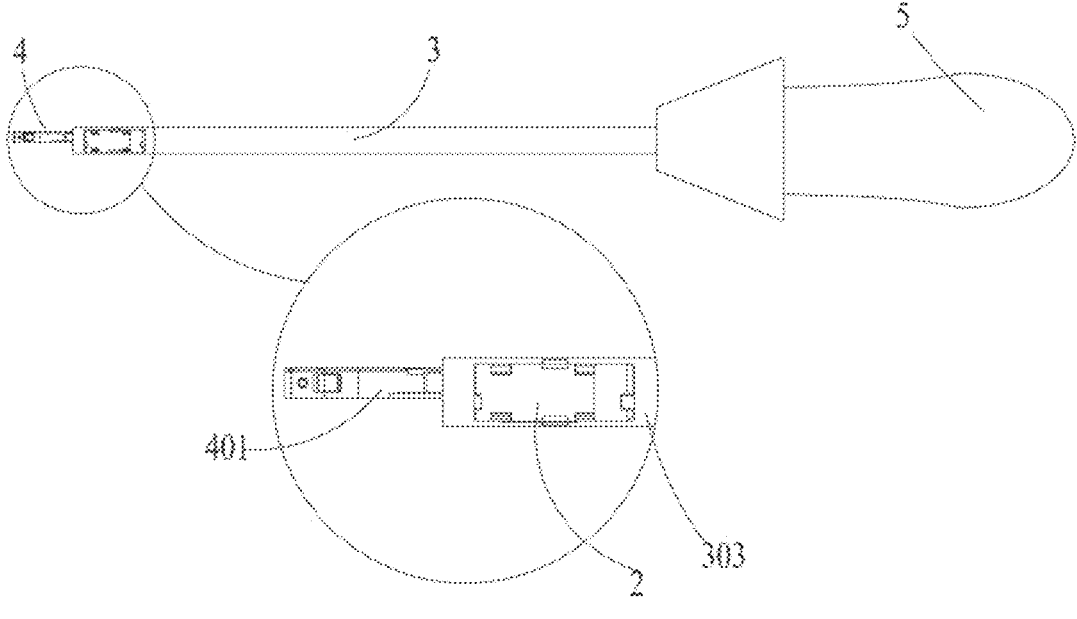
FIG. 13 is a schematic structural view of the clip applier at a second angle and provided by a specific embodiment of the present disclosure.
Figure 15:
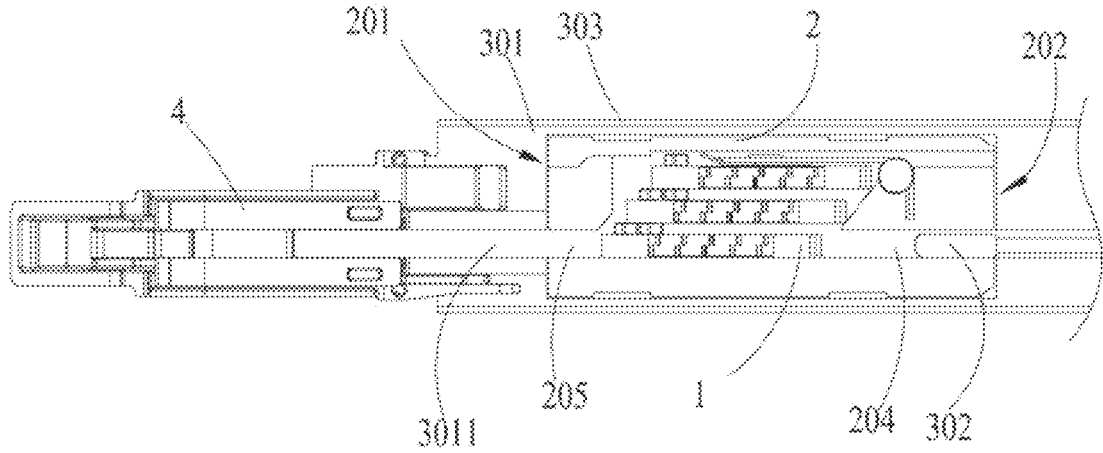
FIG. 15 is a cross-sectional view of a partial region of the clip applier provided by a specific embodiment of the present disclosure, in which a feeding rod is in an initial state.
Figure 19:
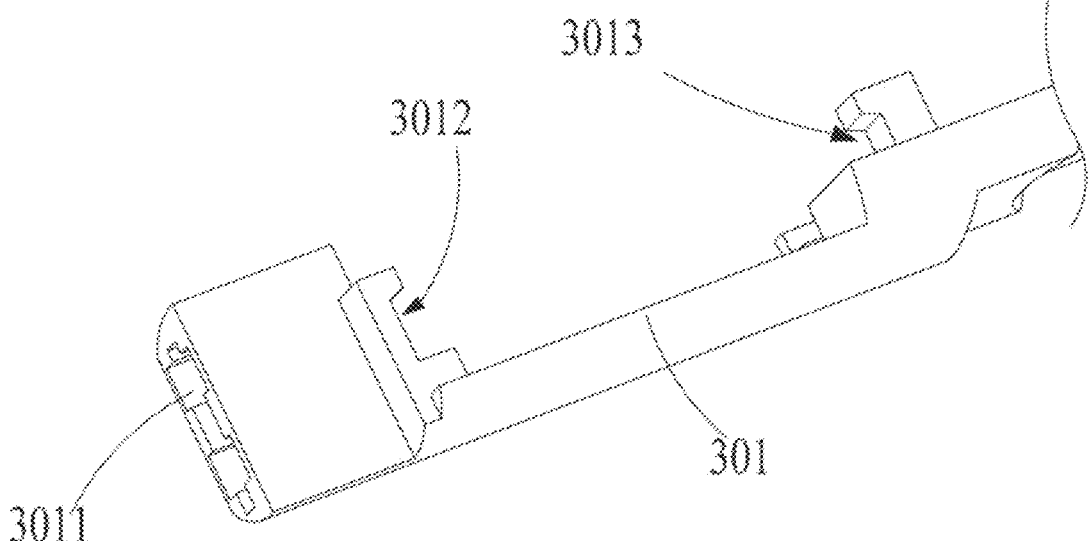
FIG. 19 is a schematic structural view of a partial region of a shaft of the clip applier provided by a specific embodiment of the present disclosure.

Referring to FIG. 12 to FIG. 14, the clip cartridge 2 is arranged on the shaft 301. The first end 201 of the clip cartridge 2 is close to the jaw assembly 4, that is to say, the first end 201 of the clip cartridge 2 is a distal end, and the second end 202 of the clip cartridge 2 is a proximal end. Referring to FIG. 15 and FIG. 19, the shaft 301 is provided with a channel 3011; and the channel 3011 is located between the jaw assembly 4 and the clip cartridge 2. The distal end of the channel 3011 leads to a region between the first jaw member 401 and the second jaw member 402; the proximal end of the channel 3011 is in communication with the first opening 205 of the second cavity 204 of the clip cartridge 2, so that the clip 1 within the second cavity 204 can enter the region between the first jaw member 401 and the second jaw member 402 through the channel 3011, and is further supported between the first jaw member 401 and the second jaw member 402.

Referring to FIG. 14, the clip cartridge 2 is connected with the shaft 301 through a buckle structure.

Figure 18:
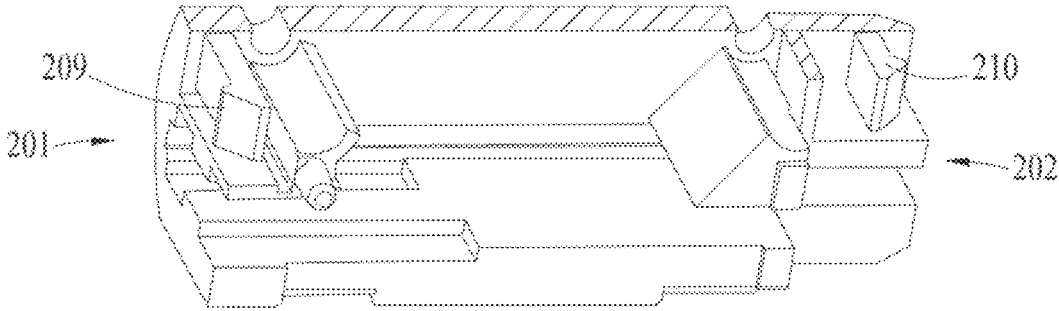
FIG. 18 is a cross-sectional view of the clip cartridge body provided by a specific embodiment of the present disclosure.

With emphasized reference to FIG. 18, the clip cartridge body is provided with a first male buckle 209 and a second male buckle 210. The first male buckle 209 is arranged at the first end 201 of the clip cartridge 2. The second male buckle 210 is arranged at the second end 202 of the clip cartridge 2.

Referring to FIG. 19, the shaft 301 is provided with a first female buckle 3012 and a second female buckle 3013. The first male buckle 209, the second male buckle 210, the first female buckle 3012, and the second female buckle 3013 constitute the buckle structure.

The first male buckle 209 is fit with the first female buckle 3012, and the first male buckle 209 can be detachably buckled with the first female buckle 3012. The second male buckle 210 is fit with the second female buckle 3013, and the second male buckle 210 is detachably buckled with the second female buckle 3013, so that the clip cartridge 2 is detachably connected with the shaft 301.

Taking the angle and the position for placing the clip applier in FIG. 13 as a reference, an axis of the rod assembly 3 of the clip applier is parallel with the second direction; the third direction is still a direction perpendicular to the paper surface; and the first direction is still the up-down direction; but the forward direction of the first direction is from bottom to top. The buckle structure between the clip cartridge 2 and the shaft 301 can limit the position of the clip cartridge 2 in the second direction and the third direction. Referring to FIG. 13 again, the sleeve 303 is sleeved on the clip cartridge 2, and the sleeve 303 can limit the position of the clip cartridge 2 in the first direction. Therefore, the clip cartridge 2 can be stably connected with the shaft 301.

A guide groove for receiving the feeding rod 302 is provided in the shaft 301; a proximal end of the feeding rod 302 is drivably connected with the handle assembly 5; the handle assembly 5 can drive the feeding rod 302 to move towards the distal end or the proximal end of the clip applier; the feeding rod 302 is flexible. A proximal end of the sleeve 303 is drivably connected with the handle assembly 5; and the handle assembly 5 can drive the sleeve 303 to move towards the distal end or the proximal end of the clip applier.

Figure 20:
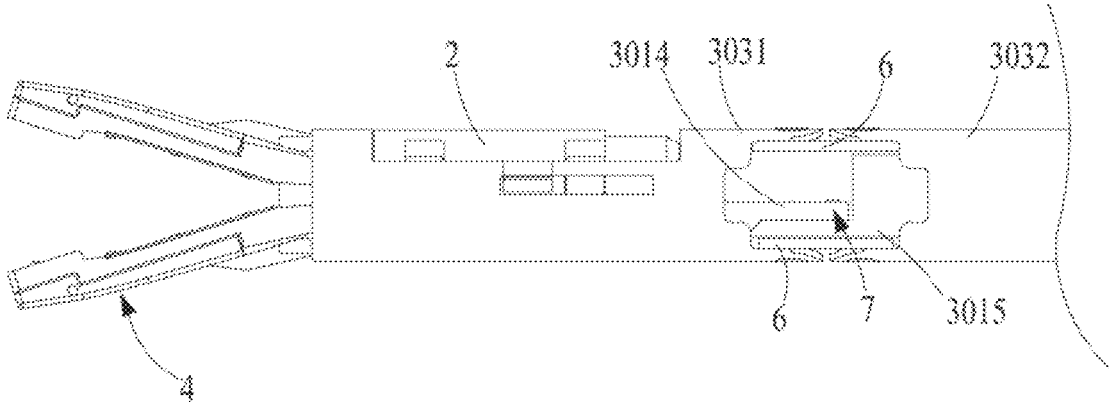
FIG. 20 is a schematic structural view of a partial region of the clip applier provided by another embodiment of the present disclosure.

The distal end of the sleeve 303 can cooperate with the jaw assembly 4. Specifically, an elastic element is arranged between the first jaw member 401 and the second jaw member 402 to keep the jaw assembly in an open state; when the sleeve 303 moves towards the distal end, the jaw assembly 4 can be received inside the sleeve 303 from the distal end of the sleeve 303; at this time, the elastic element is compressed and the jaw assembly 4 is closed. When the sleeve 303 moves towards the proximal end, the jaw assembly 4 can stretch out from the distal end of the sleeve 303, and the elastic element releases energy to open the jaw assembly 4. As shown in FIG. 14, the spring 403 can be selected as the elastic element. Referring to FIG. 20, in an optional embodiment, the clip applier has a joint 7. Specifically, the shaft 301 includes a first shaft 3014 and a second shaft 3015. The second shaft 3015 extends from the handle assembly 5. The first shaft 3014 is arranged at a distal end of the second shaft 3015. A proximal end of the first shaft 3014 is connected with the distal end of the second shaft 3015 through the joint 7, so that the first shaft 3014 can rotate relative to the second shaft 3015. The jaw assembly 4 is connected with the distal end of the first shaft 3014, so that the jaw assembly 4 can rotate relative to the second shaft 3015 as driven by the first shaft 3014, which facilitates the doctor to adjust the position and the angle of the jaw assembly 4. In this embodiment, the clip cartridge 2 is arranged at the first shaft 3014, and the clip cartridge 2 is connected with the first shaft 3014 through a buckle structure, so that the clip cartridge 2 can rotate together with the jaw assembly 4. In order to adapt to rotation of the first shaft

3014, the sleeve 303 according to this embodiment is divided into a first tube 3031 and a second tube 3032. The first tube 3031 is sleeved on the first shaft 3014 and the clip cartridge 2. The second tube 3032 is sleeved on the second shaft 3015. The first tube 3031 is connected with the second tube 3032 through two pivot members 6. A proximal end of each pivot member 6 is pivotally connected with the second tube 3032, and a distal end of each pivot member 6 is pivotally connected with the first tube 3031. Therefore, when the first shaft 3014 rotates, the first shaft 3014 drives the first tube 3031 to rotate, so that the first tube 3031 can rotate relative to the second tube 3032. Hereinafter, a clip applying process of the clip applier according to the embodiment of the present disclosure will be described.

In an initial state (i.e., when the feeding rod 302 does not push a clip), the distal end of the feeding rod 302 stretches into the second cavity 204 or does not stretch into the second cavity 204, and both structures will not affect normal use of the clip applier. If the distal end of the feeding rod 302 does not stretch into the second cavity 204 in the initial state, when the feeding rod 302 moves towards the distal end of the clip applier, the distal end of the feeding rod 302 can stretch into the second cavity 204 from the second opening 206.

Referring to FIG. 15, in this embodiment, the distal end of the feeding rod 302 stretches into the second cavity 204 in the initial state, that is, the distal end of the feeding rod 302 is arranged in the second cavity 204 in the initial state. As described above, the clip cartridge 2 includes three clips 1, namely, clip 101, clip 102 and clip 103 sequentially from top to bottom.

Figure 16:
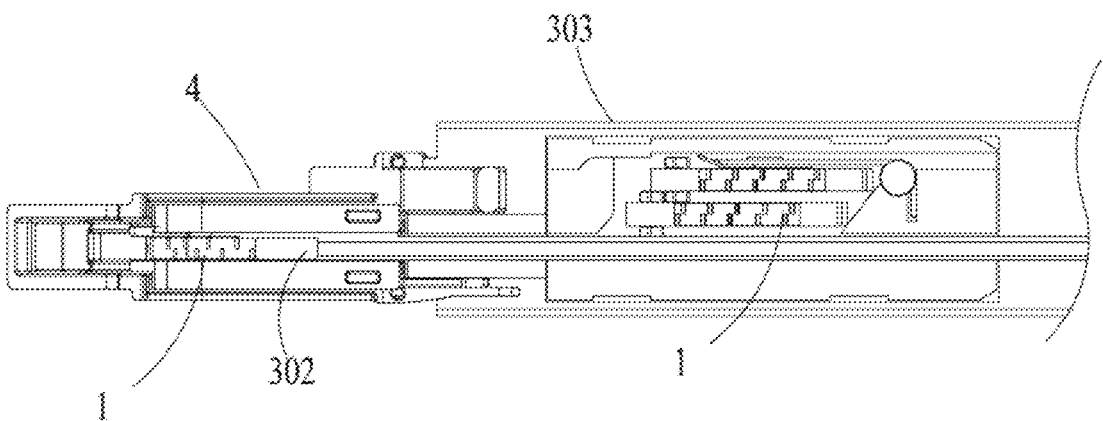
FIG. 16 is a cross-sectional view of a partial region of the clip applier provided by a specific embodiment of the present disclosure, in which the feeding rod has already fed the clip into a jaw assembly.
Figure 17:
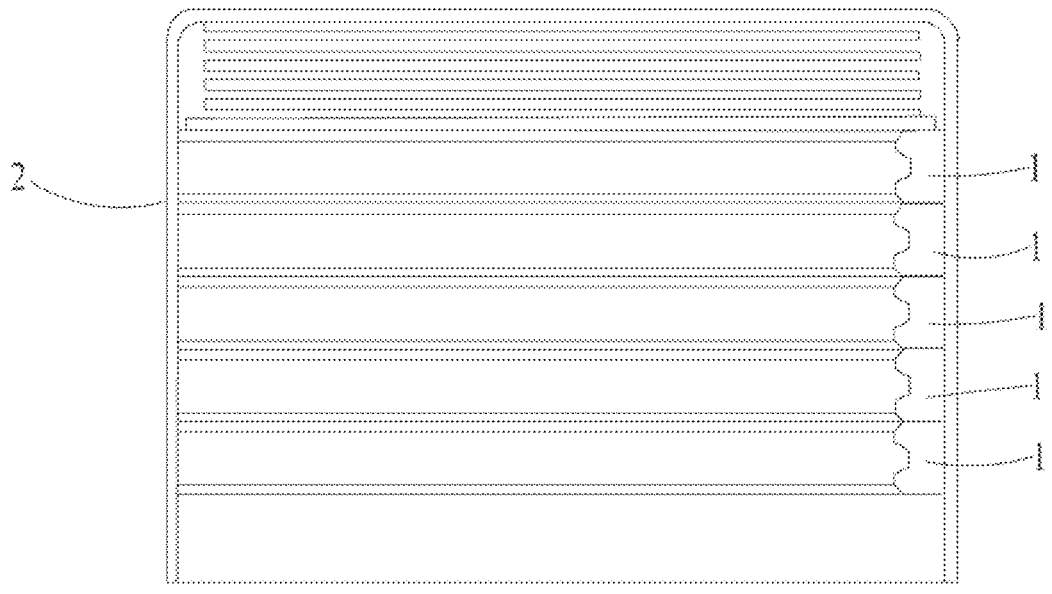
FIG. 17 is a schematic structural view of the clip cartridge in the existing art.

Referring to FIG. 16, the handle assembly 5 is manipulated to drive the feeding rod 302 to move towards the distal end of the clip applier (i.e., forward), so that the distal end of the feeding rod 302 abuts against the second end portion 110 of the clip 103 in the second cavity 204, and push the clip 103 to move in the second direction, causing the clip 103 to detach from the position limiting member 213 then detach from the second cavity 204 at the first opening 205 before entering the jaw assembly 4; at this time, the feeding rod 302 is still pushing clip 103 against the second end portion 110 of the clip 103 to prevent the clip 103 from moving towards the proximal end to cause failure of clip applying. Moreover, due to the feeding rod 302 is still in the second cavity 204, the clip 101 and the clip 102 will not move towards the second cavity 204 under an action of the bias assembly.

After the clip 103 enters the jaw assembly 4, in response to the handle assembly 5 is manipulated, the handle assembly 5 drives the sleeve 303 to move towards the distal end of the clip applier; the jaw assembly 4 is closed; and the clip 103 in the jaw assembly 4 is clamped onto an object (tissue or a blood vessel).

After the jaw assembly 4 is closed, the handle assembly 5 is manipulated; the handle assembly 5 drives the sleeve 303 to move towards the proximal end of the clip applier (i.e., backward); the jaw assembly 4 is opened and the clip 103 detaches from the jaw assembly 4.

After the clip 103 detaches from the jaw assembly 4, in response to the handle assembly 5 is manipulated; the handle assembly 5 drives the feeding rod 302 to move towards the proximal end of the clip applier, causing the feeding rod 302 to move towards the proximal end for reset. After the feeding rod 302 is reset, As a result of the bias assembly, the second end portion 110 of the clip 101 in the first cavity 203 moves along the position limiting slope 214, and the second end portion 110 of the clip 102 moves along the position limiting slope 214; both the clip 101 and the clip 102 have downward and forward movement, and the clip 102 moves into the second cavity 204. According to the above-described clip applying process of the clip 103, the clip 102 is applied. After the clip 102 detaches from the jaw assembly 4, the bias assembly moves the clip 101 in the first cavity 203 into the second cavity 204, and then continues to apply the clip 101.

As described above, in this embodiment, with respect to the three clips 1 in the clip cartridge body, the second end portions 110 thereof are not aligned; the second end portion 110 of the clip 101 is closest to the second end 202 of the clip cartridge 2, and the second end portion 110 of the clip 103 is farthest from the second end 202 of the clip cartridge 2. If there is no position limiting slope 214, in the initial state, that is, when no clip is applied to the jaw assembly, the second end portion 110 of the clip 102 will fall into the second cavity 204 and block the second end portion 110 of the clip 103, when the feeding rod 302 moves towards the proximal end, it abuts against the second end portion 110 of the clip 102 and fails to abut against the second end portion 110 of the clip 103, so that the clip applier cannot be used normally. Similarly, when applying the clip 102, the second end portion 110 of the clip 101 will fall into the second cavity 204, and the feeding rod 302 fails to abut against the clip 102. In this embodiment, the position limiting slope 214 is arranged inside the first cavity 203, the position limiting slope 214 can support the clip 1 inside the first cavity 203; the clip 101 and the clip 102 can be arranged substantially in the second direction. The second end portion 110 of the clip 102 will not fall into the second cavity 204, and thus will not affect use of the clip 103. Similarly, when applying the clip 102, the second end portion 110 of the clip 101 will not fall into the second cavity 204, and the feeding rod 302 can push the clip 102 to the jaw assembly 4.

In summary, in this embodiment, by stacking the clips 1 in a staggered manner, space can be saved; and the protruding portions of adjacent clips 1 can avoid each other, so that the clips 1 can be stably stacked in the clip cartridge 2.

It should be understood that although the specification is described according to the embodiments, not each embodiment only includes an independent technical solution; such description in the specification is for clarity only. Those skilled in the art should treat the specification as a whole, and the technical solutions in respective embodiments can be appropriately combined to form other embodiments that those skilled in the art can understand.

The series of detailed illustrations as listed above are only specific illustrations for the feasible embodiments of the present disclosure, and are not intended to limit the protection scope of the present disclosure. Any equivalent embodiment or change without departing from the spirit of the present disclosure should be included in the protection scope of the present disclosure.

The invention claimed is:

1. A clip cartridge, comprising:
    at least two clips, wherein each of the at least two clips comprises a clip leg, the clip leg has a protruding portion, the clip cartridge further comprises:
    a clip cartridge body, wherein the clip cartridge body has at least one clip cavity to receive the clips, the at least two clips are stacked in a first direction in a staggered manner, so that protruding portions of adjacent clips are staggered in the first direction, each clip is arranged substantially in a second direction;
    wherein the at least one clip cavity comprises a first cavity and a second cavity that are sequentially arranged in the first direction, and in an initial state, both the first cavity and the second cavity receive the clips.

2. The clip cartridge according to claim 1, wherein each clip leg has two sidewalls opposite to each other in the first direction, and at least one of the sidewalls has the protruding portion.

3. The clip cartridge according to claim 1, wherein the clip cartridge further comprises a bias assembly, the bias assembly is arranged in the clip cartridge body, and the bias assembly is configured to apply a force on the clips substantially in the first direction.

4. The clip cartridge according to claim 3, wherein the bias assembly comprises an elastic member.

5. The clip cartridge according to claim 4, wherein the bias assembly further comprises a push plate, the push plate is configured to abut against the clips in a forward direction along the first direction, and the push plate is configured to apply the force on the clip in the first direction under an action of the elastic member.

6. The clip cartridge according to claim 3, wherein the bias assembly is configured to abut against a first clip in a forward direction along the first direction.

7. The clip cartridge according to claim 1, wherein the clip leg has two sidewalls opposite to each other in the first direction, at least one of the sidewalls is provided with the protruding portion, each of the clips comprises a first end portion and a second end portion, the protruding portion is close to the first end portion and away from the second end portion, the first cavity is provided therein with a position limiting slope, and the position limiting slope is configured to abut against the second end portion of the clip in the first cavity.

8. The clip cartridge according to claim 4, wherein the clip leg has two sidewalls opposite to each other in the first direction, at least one of the sidewalls is provided thereon with the protruding portion, the second cavity has a groove extending in the second direction, and the protruding portion of the clip located in the second cavity is received in the groove.

9. The clip cartridge according to claim 4, wherein the clip cartridge has a first end and a second end opposite to each other in the second direction, the second cavity extends in the second direction, the second cavity forms a first opening at the first end of the clip cartridge, and the second cavity forms a second opening at the second end of the clip cartridge.

10. The clip cartridge according to claim 9, wherein the clip cartridge body comprises a position limiting member, the position limiting member is arranged on a sidewall of the clip cartridge body, the position limiting member is configured to abut against the clip located in the second cavity, and in response to a force applied in the second direction on the clip, the clip is configured to detach from the position limiting member and is configured to detach from the second cavity at the first opening.

11. The clip cartridge according to claim 1, wherein the first cavity is in communication with the second cavity.

12. The clip cartridge according to claim 11, wherein a third opening is arranged at an upper wall portion of the second cavity at a position corresponding to the first cavity, the second cavity is in communication with the first cavity through the third opening.

13. A clip applier, comprising a handle assembly, a rod assembly, and a jaw assembly, wherein the rod assembly extends from the handle assembly, the jaw assembly is provided at a distal end of the rod assembly, wherein the clip applier further comprises the clip cartridge according to claim 1, and the clip cartridge is provided at the rod assembly.

14. The clip applier according to claim 13, wherein the clip cartridge is connected with the rod assembly through a buckle structure.

15. The clip applier according to claim 13, wherein the rod assembly comprises a shaft, the shaft comprises a first shaft and a second shaft that are connected through a joint, so that the first shaft is capable of rotating relative to the second shaft, and the jaw assembly is connected with a distal end of the first shaft.

16. The clip cartridge according to claim 15, wherein clip cartridge is arranged at the first shaft.

17. The clip applier according to claim 13, wherein the at least one clip cavity comprises a first cavity and a second cavity that are sequentially arranged in the first direction, and in an initial state, both the first cavity and the second cavity receive the clips, the clip cartridge has a first end and a second end opposite to each other in the second direction, the second cavity extends in the second direction, the second cavity forms a first opening at the first end of the clip cartridge, and the second cavity forms a second opening at the second end of the clip cartridge.

18. The clip applier according to claim 17, wherein the rod assembly comprises a shaft, the jaw assembly includes a first jaw member and a second jaw member that are pivotally connected with the shaft, respectively, the shaft is provided with a channel, and the channel is located between the jaw assembly and the clip cartridge, a distal end of the channel leads to a region between the first jaw member and the second jaw member, a proximal end of the channel is in communication with the first opening of the second cavity of the clip cartridge.

19. A clip cartridge, comprising:

at least two clips, wherein each of the at least two clips comprises a clip leg, the clip leg has a protruding portion, the clip cartridge further comprises:

a clip cartridge body, wherein the clip cartridge body has at least one clip cavity to receive the clips, the at least two clips are stacked in a first direction in a staggered manner, so that protruding portions of adjacent clips are staggered in the first direction, each clip is arranged substantially in a second direction;

wherein the clip cartridge further comprises a bias assembly, the bias assembly is arranged in the clip cartridge body, and the bias assembly is configured to apply a force on the clip substantially in the first direction, wherein the bias assembly comprises an elastic member;

wherein the bias assembly further comprises a push plate, the push plate is configured to abut against the clips in a forward direction along the first direction, and the push plate is configured to apply the force on the clips in the first direction under an action of the elastic member, wherein the elastic member comprises a first torsion arm, a second torsion arm, and a spiral body that are integrated, and wherein a mounting block is further provided with a mounting groove, the first torsion arm is arranged inside the mounting groove, and the second torsion arm is twisted around the spiral body and is arranged on an upper side of the clips and connected with the push plate, the second torsion arm is configured to apply the force on the clips substantially in the first direction through the push plate.

20. The clip cartridge according to claim 19, wherein the at least one clip cavity comprises a first cavity and a second cavity that are sequentially arranged in the first direction, and in an initial state, both the first cavity and the second cavity receive the clips.

\* \* \* \* \*